United States Patent [19]
Zdrojkowski et al.

[11] 4,087,840
[45] May 2, 1978

[54] METHOD AND APPARATUS FOR MAGNETICALLY RECORDING AND REPRODUCING PHYSIOLOGICAL INFORMATION

[75] Inventors: Ronald J. Zdrojkowski; Richard L. Longini, both of Pittsburgh, Pa.

[73] Assignee: Carnegie-Mellon University, Pittsburgh, Pa.

[21] Appl. No.: 696,717

[22] Filed: Jun. 16, 1976

[51] Int. Cl.² .............................................. G11B 5/09
[52] U.S. Cl. ........................................ 360/41; 360/43
[58] Field of Search ................. 360/18, 39, 40, 41, 360/43, 51

[56] References Cited
U.S. PATENT DOCUMENTS

| | | | |
|---|---|---|---|
| 3,562,724 | 2/1971 | Adler | 360/41 |
| 3,699,554 | 10/1972 | Jones | 360/43 |
| 3,719,934 | 3/1973 | Behr et al. | 360/41 |
| 3,761,906 | 9/1973 | Finster et al. | 360/51 |

FOREIGN PATENT DOCUMENTS

419,960  8/1974  U.S.S.R. ................. 360/53

*Primary Examiner*—Jay P. Lucas
*Attorney, Agent, or Firm*—Fleit & Jacobson

[57] ABSTRACT

Disclosed are a method and an apparatus for magnetically recording and reproducing physiological information such as in an electrocardiogram. The ECG signal is pulse width modulated (PWM), and the transition points, or zero crossings are stored on magnetic tape. The original PWM signal is then reproduced from the output of the playback head by reacting to the simultaneous occurrence of zero crossings and large magnitude derivative signals. Also disclosed is the concept of automatically reacting to recorded audible information during the reconstruction of the original PWM signal.

6 Claims, 10 Drawing Figures

METHOD AND APPARATUS FOR MAGNETICALLY RECORDING AND REPRODUCING PHYSIOLOGICAL INFORMATION

BACKGROUND OF THE INVENTION

The present invention relates broadly to a method and an apparatus for accurately reproducing pulse width modulated (PWM) signals represented on magnetic tape. More specifically, the present invention relates to the magnetic recording and reproduction of physiological information, such as in electro-cardiograms, in PWM format.

Pulse width modulation is sometimes utilized in magnetic tape recording wherein the range of frequencies to be recorded has only a moderate passband, for example from DC to some low frequency. Recording in PWM format is advantageous because playback can be accomplished with substantial fidelity. However, PWM techniques have some serious disadvantages when compared with frequency modulation techniques.

Because recorded magnitudes and playback magnitudes cannot be precisely held, it is impractical to record the entire PWM signal on tape. It is therefore common in recording PWM information, to record only the level transitions, or zero crossings, on magnetic tape. One standard method is to record a narrow pulse at each level transition of the PWM signal. For example, a recorded positive pulse could represent a positive-going level transition of the original PWM signal, while a negative pulse could represent a negative-going transition.

If the position of the transitions could be determined with precision, there would be no difficulty in precisely reconstructing the original PWM signal. There are, however, substantial problems in precisely determining the level transitions of the original PWM input signal.

Ideally, the voltage on the playback head would indicate zero crossings only at the desired level transitions, corresponding to the pulses recorded by the recording head. Also, the slope of voltage versus time is ideally quite steep in the neighborhood of the desired zero crossings, with the slope at each zero crossing having the same magnitude. The recording level is also ideally uniform.

In practice, the foregoing desirable and ideal conditions do not exist. Rather, random noise produces zero crossings on the playback head at other than the desired zero crossings which represent actual PWM level transitions. The slope of voltage versus time at the zero crossings is not so steep as is desired, nor are the slopes of all zero crossings identical. Furthermore, the overall signal amplitude frequently varies as by reason of nonuniformities in the properties of the magnetic tape, and the uniformity of tape speed is also to be considered.

It is the problem of the precise determination of level transitions in PWM signals and the solution to this problem that the present invention is directed.

SUMMARY OF THE INVENTION

The present invention relates to a method and an apparatus for reconstructing magnetically recorded PWM signals, especially those containing physiological information such as in electrocardiograms. Basically, the present invention relates to reproducing magnetically recorded PWM information by tracking the voltage on the playback head of a tape recorder and reacting to the simultaneous occurrence of a zero crossing and a large derivative signal.

When playing back the magnetically recorded pulse train representing the actual level transitions of a PWM signal, the zero crossings of the signal on the playback head have relatively steep wave fronts. Therefore, the derivative of the playback head signal is relatively large at the times of the desired zero crossings. And, when analyzing the signal on the playback head, it can be seen that there is an absence of spurious zero crossings in the immediate vicinity of the zero crossings which represent actual level transitions. This is the case because of the relatively large amplitude of the signal before and after the desired zero crossing.

In the inventive system, ECG signals are developed, as by an ECG amplifier, and are then converted into PWM format. The PWM information is then fed to the recording head of a tape recorder, which naturally takes a derivative, and positive-going and negative-going pulses are recorded on the tape which correspond in time to the level transitions in the original PWM signal. In reconstructing the PWM information recorded on tape, the voltage output of the playback head is a time derivative of the recorded pulses, but includes not only the desired zero crossings at the recorded pulses, but also spurious zero crossings resulting from noise factors and the like.

In order to eliminate the effects of the spurious zero crossings, the invention contemplates simultaneously detecting the zero crossings in the playback head signal and large magnitudes in the time derivative signal. In view of the absence of spurious zero crossings in the vicinity of the desired zero crossings, the time derivative signal is of large magnitude only when responding to the desired zero crossings. The precise instants of the desired zero crossings are then triggered by outputs from a zero crossing detector circuit. The spurious zero crossings in the voltage on the playback head are ignored. And, since triggering at the instant of the zero crossing, the reproduced PWM signal is substantially identical to the original signal.

As a further advance, the present invention relates to the concept of interspersing voice communication in the recorded PWM information, at the command of an operator. In particular, it is contemplated that the PWM information be carried on a carrier of, for example, 400 Hz. Upon actuation by the operator, the 400 Hz carrier signal is discontinued, and voice information is re-corded on the magnetic tape. Then, in the playback mode, provision is made for muting an audio amplifier when the 400 Hz carrier is detected. When the 400 Hz carrier is absent, however, as when the operator was recording voice information on the tape, the audio amplifier is enabled, and the voice of the operator can be heard over a speaker system. At the end of the voice communication, when the operator's microphone is disenabled, the 400 Hz carrier again appears on the tape and mutes the audio amplifier.

It is accordingly the principal object of the present invention to provide a method and an apparatus for magnetically recording and accurately reproducing pulse width modulated signals.

A more specific object of the present invention is to provide a method and an apparatus for magnetically recording physiological information, such as in an electrocardiogram, in PWM format and accurately reproducing such information.

Another object of the present invention is to provide an apparatus for magnetically recording and accurately reproducing physiological information, as in an electrocardiogram, which is relatively simple and inexpensive.

Still a further object of the present invention is to provide a method and an apparatus for reproducing magnetically recorded PWM signals by sensing the simultaneous occurrence of zero crossings and high amplitude derivative signals from a playback head.

Another object of the present invention is to provide a method and an apparatus for defining the instant of a zero crossing in a signal by triggering when a zero crossing occurs during a large derivative period.

Yet a further object of the present invention is to provide a logic system which utilizes the simultaneous outputs of a zero crossing detector and a high amplitude derivative detector to indicate the occurrence of zero crossings in a signal.

Another object of the present invention is to provide a pulse width modulated magnetic recorder wherein zero crossings in the recorded information are determined by the occurrence of zero crossing signals during large derivative periods, the determination being made at the instant of the zero crossings.

A further object of the present invention is to provide a mechanism whereby magnetically recorded PWM information can accurately be reproduced, and wherein audio information can be interspersed on the magnetic tape at the command of the operator.

These and other objects of the present invention, as well as many of the attendant advantages thereof, will become more readily apparent when reference is made to the following description, taken in conjunction with the accompanying drawings.

DETAILED DESCRIPTION OF THE DRAWINGS

Figure 1:
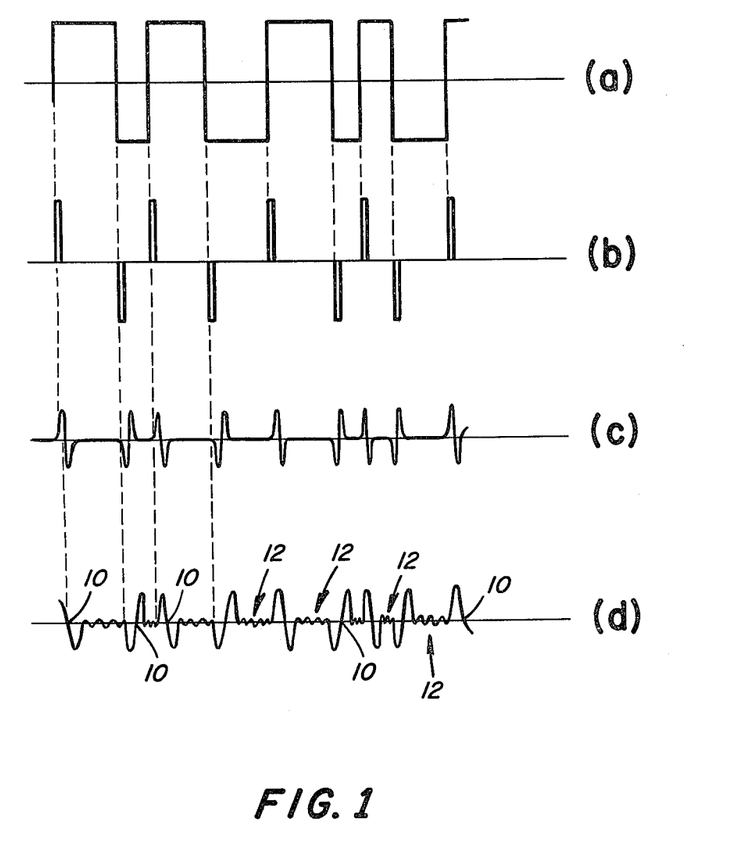
FIG. 1, consisting of a through d, illustrates ideal and typical waveforms to explain the concept of recording PWM information on magnetic tape and reproducing the same.

With reference first to FIG. 1, the principle of recording pulse width modulated (PWM) information on magnetic tape and reproducing the same from the magnetic tape will be described. As noted above, it is not practical to record and directly play back the PWM signal. Therefore, narrow pulses corresponding to the respective changes in amplitude of the original PWM signal are recorded.

FIG. 1(a) illustrates the original PWM signal which is to be recorded on magnetic tape and then reproduced from the tape. FIG. 1(b) shows the signal which is derived from the original PWM signal of FIG. 1(a) and recorded on the tape through the means of a conventional recording head. As can be seen when comparing FIGS. 1(a) and 1(b), a positive pulse is recorded on the tape at each occurrence where the PWM signal encounters a level transition from negative to positive, and a negative pulse is recorded for each negative-going transition.

The recorded pulses illustrated in FIG. 1(b) are quite narrow, and therefore the voltage output signal of the playback head, which is the natural derivative of the recorded signal, will ideally resemble the signal shown in FIG. 1(c). The zero crossings of the ideal playback signal of FIG. 1(c) correspond to the respective centers of the recorded pulses which, in time, correspond to the level transitions of the original PWM signal. It should of course be appreciated that the recording and playback of the PWM signal occur at different times and that the representations of FIGS. 2(b) and 2(c) are superimposed in time for purposes of illustration and to facilitate understanding.

The original PWM signal of FIG. 1(a), recorded in the form of pulses as shown in FIG. 1(b), is ideally reconstructed by detecting the precise zero crossings of the playback signal of FIG. 1(c), and then generating a square or rectangular wave whose level transitions occur in time simultaneous with such zero crossings. The major practical problem in such a PWM recording and playback system is the precise determination of zero crossings. For the curve of FIG. 1(c) is an ideal playback signal; the waveform encountered in practice is illustrated in FIG. 1(d). And as can be seen in FIG. 1(d) the signal derived from the playback head contains not only the desired zero crossings which represent the actual level transitions in the original PWM signal, but many other spurious zero crossings. In practice, therefore, it is imperative that an effective PWM record and playback system have the capability of ignoring the spurious, low amplitude noise pulses, and reacting only to the high amplitude information pulses when reproducing a PWM signal.

Figure 2:
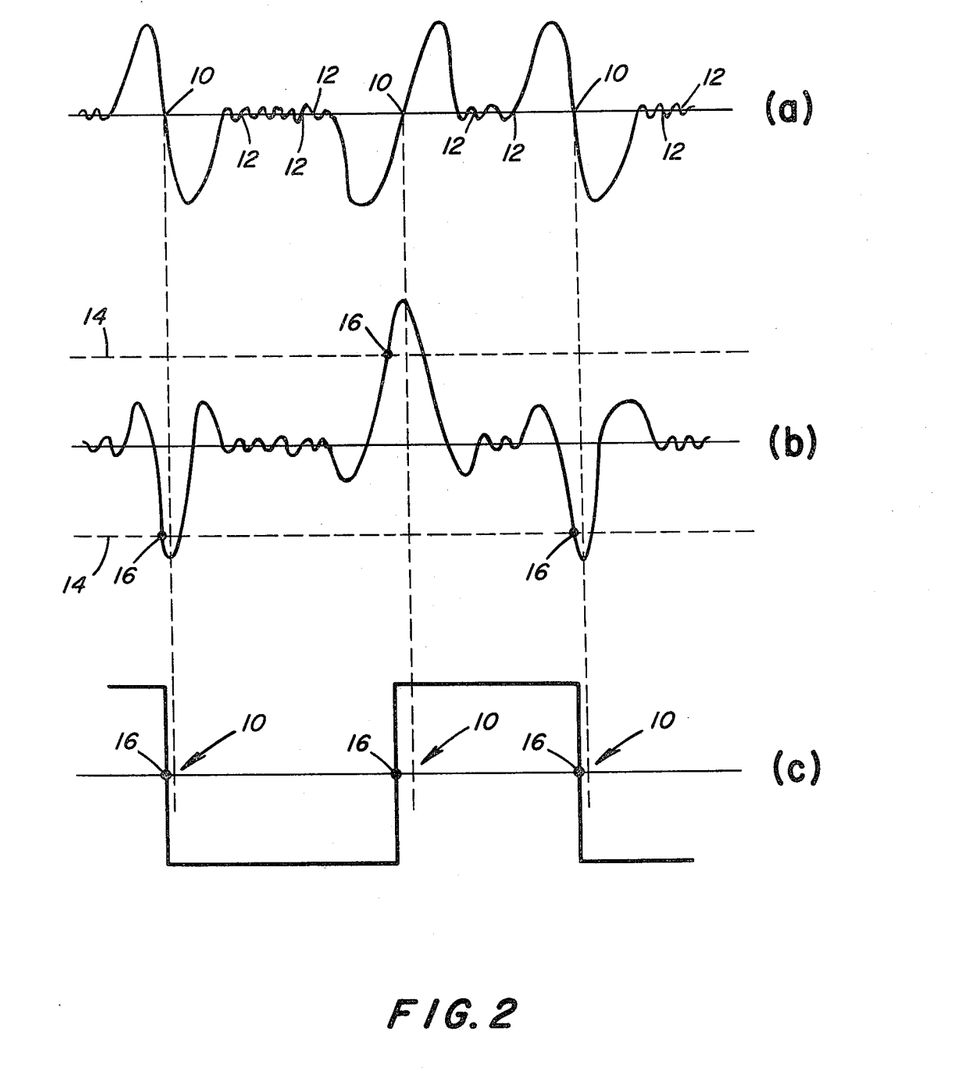
FIG. 2, consisting of a through c, illustrates voltage curves representing a known technique of reproducing PWM signals from magnetic tape.

A known and effective demodulation scheme for discriminating between the desired and the spurious zero crossings when reproducing PWM signals can be seen in FIG. 2. This technique utilizes a time derivative of the playback signal, through a threshold detector, to trigger a flip-flop circuit which produces a rectangular wave similar to the original PWM signal. The original PWM signal and the recorded pulse train are not here illustrated, but reference can again be made to FIGS. 1(a) and 1(b). The playback signal derived from the playback head can be seen in FIG. 2(a), which is substantially identical to the curve shown in FIG. 1(d). The time derivative of the playback signal, derived by well known techniques, is shown in FIG. 2(b). The maximum rate of change of the playback signal, as can be seen in FIG. 2(a), occurs at the zero crossings, and hence the FIG. 2(b) derivative signal peaks at these same instants. This can also be seen by referring back to FIGS. 1(a) and 1(d). Some zero crossings of the playback signal correspond to actual transitions of the original PWM signal, and are shown at 10 in FIG. 2(a), while the spurious zero crossings, of far lesser amplitude, are shown at 12.

Since the high amplitude peaks of the derivative signal accurately correspond in time to the desired zero crossings of the playback signal, a detector circuit which can accurately respond to these peaks could precisely reproduce the original PWM signal. However, no such detector exists in practice since the slopes at the zero crossings of the playback signal are not uniform. Therefore, the amplitude of the peaks in the corresponding derivative signal also varies. Level detector, or threshold circuits are accordingly utilized in practice. The threshold levels of such circuits are represented in FIG. 2(b) at 14. As can be seen, the threshold 14 is set below the lowest desired peak amplitude and above the highest amplitude expected for spurious zero crossings. With such a playback circuit, as illustrated in FIG. 2(c), the flip-flop would be triggered at the instant the derivative signal crossed the threshold 14, rather than at the precise zero crossings. The trigger times are shown at 16, and as can be seen by comparing FIGS. 2(a) and 2(c), lead the actual events, the zero crossings 10, by a time dependent upon the shape of the derivative signal peak. The corresponding reconstructed PWM waveform is illustrated in FIG. 2(c).

Figure 3:
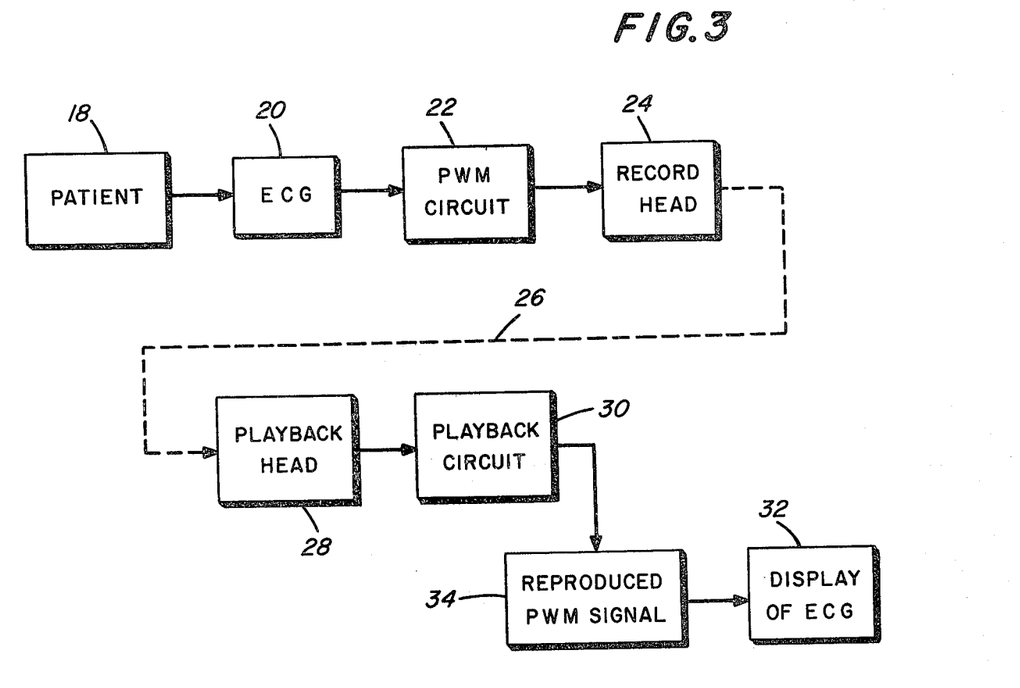
FIG. 3 is a simplified block diagram of the inventive circuit including both the recording and the playback portions thereof.

With reference now to FIG. 3, a generalized block diagram of the present invention will be described. Here, the present invention is illustrated as a complete system for detecting, recording on tape, reproducing and then displaying ECG information. The patient under study is represented at block 18, and associates with an ECG circuit 20. Circuit 20 is conventional, and serves to sense the electrical activity of the patient's heart and develop an analog electrical output signal representative thereof. The output of the ECG circuit 20 is fed to a pulse width modulation circuit 22, wherein the ECG signals are converted into PWM format. The PWM information representative of the patient's ECG is then recorded on tape in the form of pulses such as those shown in FIG. 1(b), by associating with recording head 24. The remainder of the magnetic tape recording system is not shown, but is conventional.

When it is desired to display the patient's ECG, the previously recorded information on the magnetic tape is played back as illustrated by phantom line 26. The playback head can be seen at 28, and reacts to the recorded pulses as in FIG. 1(b) by producing an output signal as in FIG. 1(d). Then, by means of the inventive playback circuit 30 to be described in detail in the following paragraphs, the playback signal of FIG. 1(d) is accurately reproduced as the original PWM signal shown in FIG. 1(a). The reproduced PWM signal is then converted into analog format, and visually displayed as by paper tracing or an oscilloscope screen. This is indicated in FIG. 3 at block 32.

The accuracy of reproduction of ECG information is of primary importance. Therefore, frequency modulation is typically employed when magnetically recorded ECG information is to be reproduced for subsequent display. The inventive playback circuit 30 enables the use of PWM techniques in magnetic recording and subsequent accurate playback of ECG information.

Figure 4:
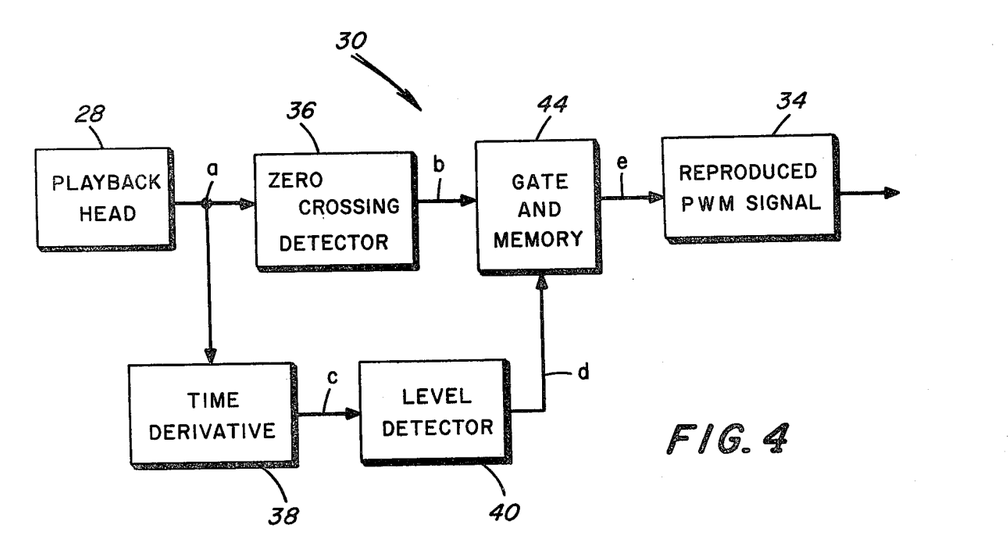
FIG. 4 is a more detailed block diagram of the playback portion of the inventive circuit.
Figure 5:
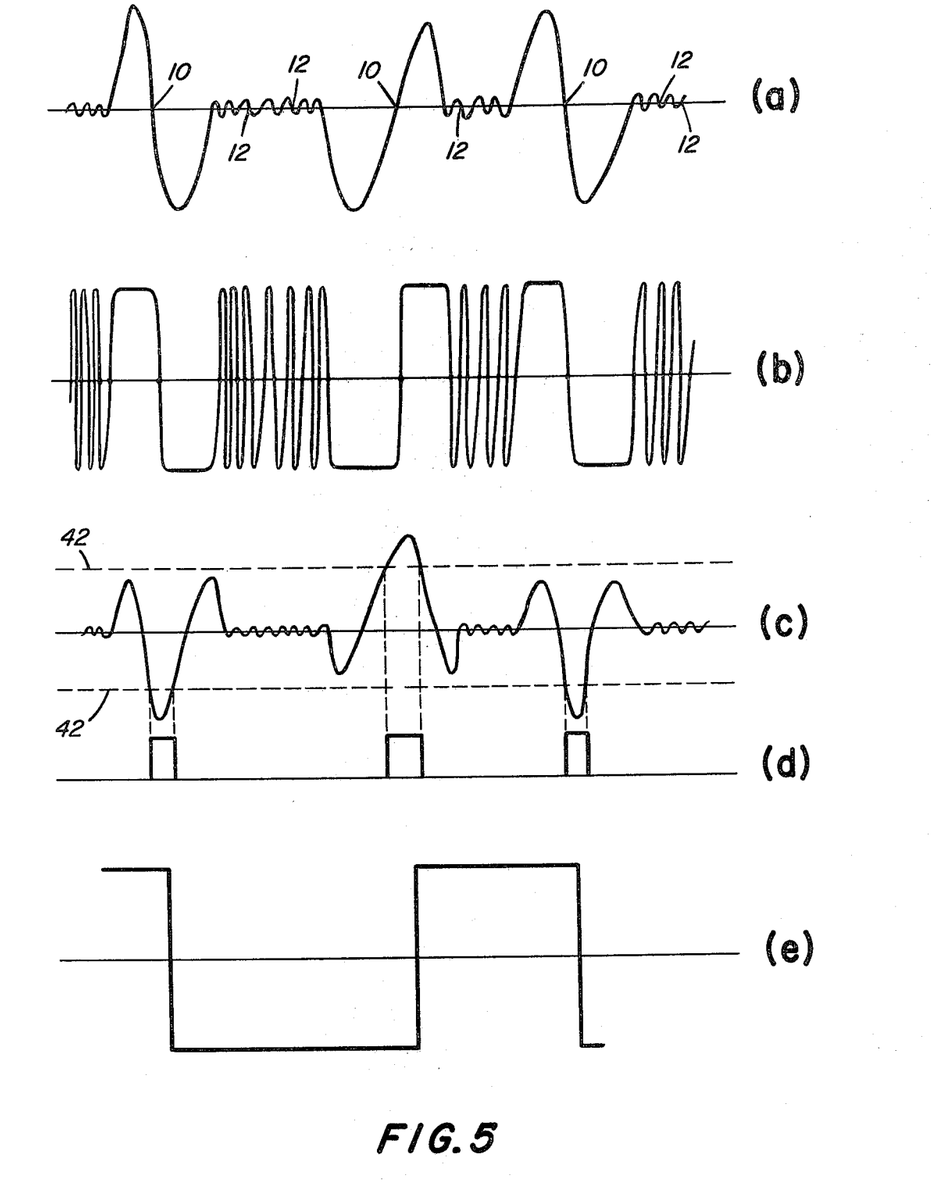
FIG. 5, consisting of a through e, illustrates voltage signals at various locations in the block diagram shown in FIG. 4.

With reference now to FIG. 4, a block diagram of the inventive playback circuit 30 will be described. Typical voltage waveforms at selected locations in the circuit of FIG. 4 are illustrated in FIG. 5, and should also be considered.

As noted previously, the ECG information is stored on magnetic tape in the form of pulses shown in FIG. 1(b). These recorded pulses are converted by the playback head 28 into a derivative signal which appears at "a" in FIG. 4 and which is illustrated in FIG. 5(a). It should be recalled that this derivative signal has a direct relationship to the original PWM signal, with zero crossings 10 corresponding in time to the actual level transitions in the original PWM signal. Zero crossings 12 are spurious, and result from undesirable interference such as noise. This derivative signal "a" is simultaneously applied to a zero crossing detector 36 and a time derivative circuit 38.

The zero crossing detector 36 is a comparator which changes states at the instant of each zero crossing in the playback signal "a" from head 28. The output of the zero crossing detector 36 appears at "b" in FIG. 4 and is depicted in FIG. 5(b) as a train of constant amplitude pulses, the leading edges of which correspond in time to the zero crossings of playback signal "a". The output "b" of detector 36 therefore depicts both the desired and spurious zero crossings of the playback signal.

The playback signal from head 28 also serves as the input to the time derivative circuit 38. Circuit 38 takes the derivative of its input signal, and issues an output at "c" in FIG. 4, the derivative signal being illustrated in FIG. 5(c). This derivative signal is then fed to a level detector, or threshold circuit 40. The level detector circuit 40, with a preset threshold value, issues an output signal which changes state each time the derivative signal from circuit 38 exceeds a threshold level. The thresholds are shown at 42 in FIG. 5(c). As can be seen in FIGS. 5(a) through 5(d), since only the desired zero crossings generate derivatives which exceed threshold 42, the level detector circuit 40 serves to classify the zero crossings in the playback signal as desired zero crossings or spurious zero crossings. The desired zero crossings trigger level detector circuit 40 to issue pulses, while the spurious zero crossings do not. The output of detector circuit 40 appears in FIG. 4 at "d" and is illustrated by the pulse train of FIG. 5(d). The output of the level detector circuit 40 is fed to and affects the state of a gate and memory circuit 44, the other input of which is from the zero crossing detector 36. The presence of an input pulse from detector 40 to the gate and memory circuit 44 opens a gate in circuit 44.

The operation of the gate and memory circuit 44 is such that its output at "e" in FIG. 4 and as shown in FIG. 5(e), follows the output of the zero crossing detector 36 when the gate 44 is open. When the output of detector 40 falls to zero and the gate of circuit 44 closes, the memory output of circuit 44 remains at the level it held when the gate closed. Therefore, the output of memory circuit 44, shown in FIG. 5(e) changes state only at the precise times of the desired zero crossings of the original playback signal of FIG. 5(a), as triggered by the output of zero crossing detector 36. The gate 44 is open only when the derivative of the playback signal is large. In the example illustrated above, this large derivative (exceeding the threshold) occurs only within the region of the desired zero crossings. Therefore the spurious zero crossings are not detected. In an example to follow, spurious zero crossings are detected, but do not affect the accuracy of the inventive circuit. The reproduced PWM output signal is issued as shown in FIG. 4 at 34.

Figure 6:
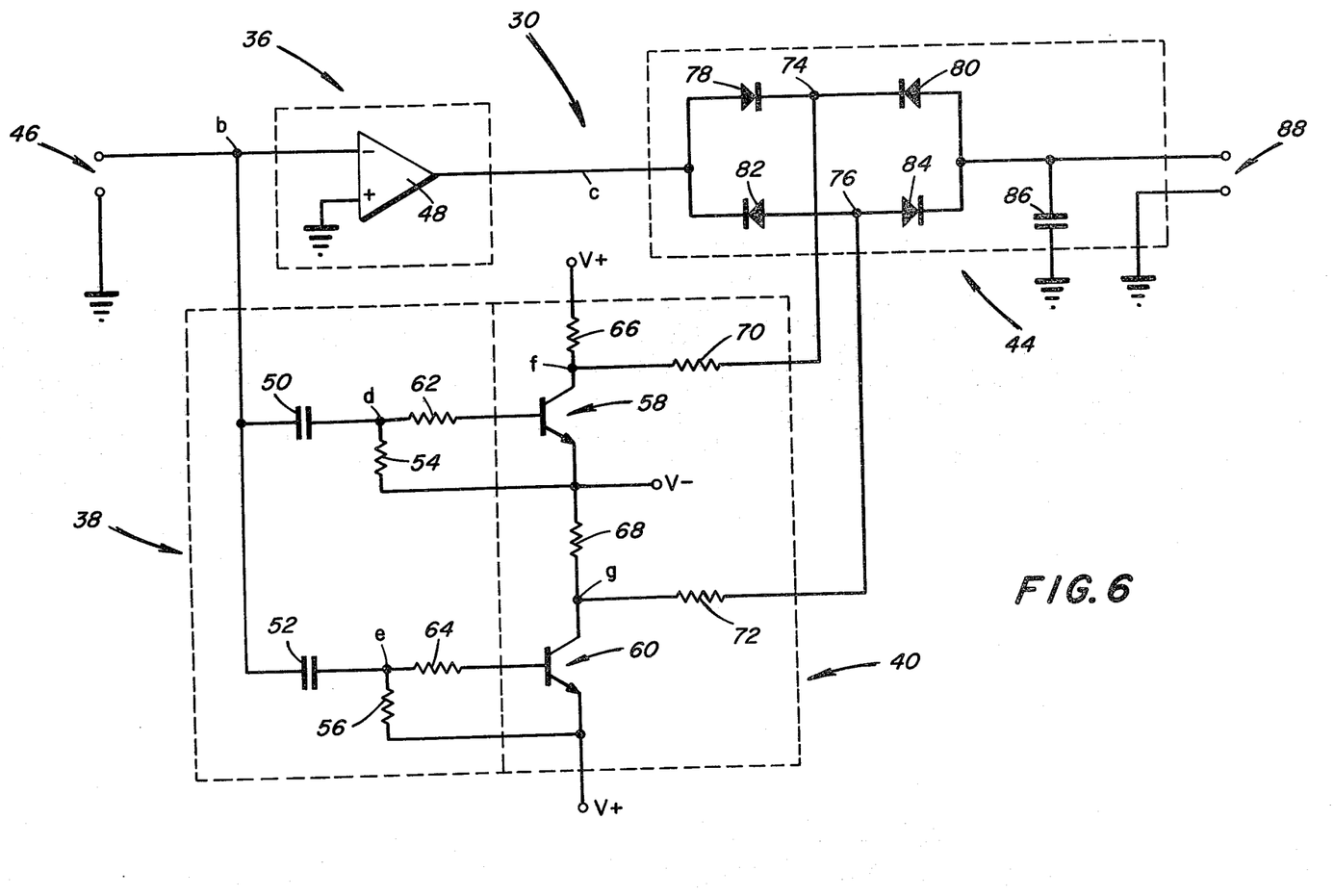
FIG. 6 is a circuit schematic illustrating a part of the playback portion of the inventive circuit.

A specific circuit diagram of the playback circuit 30 forming a part of the present invention is illustrated in FIG. 6. The voltage waveforms at various locations in the circuit of FIG. 6 are shown in FIG. 7.

Figure 7:
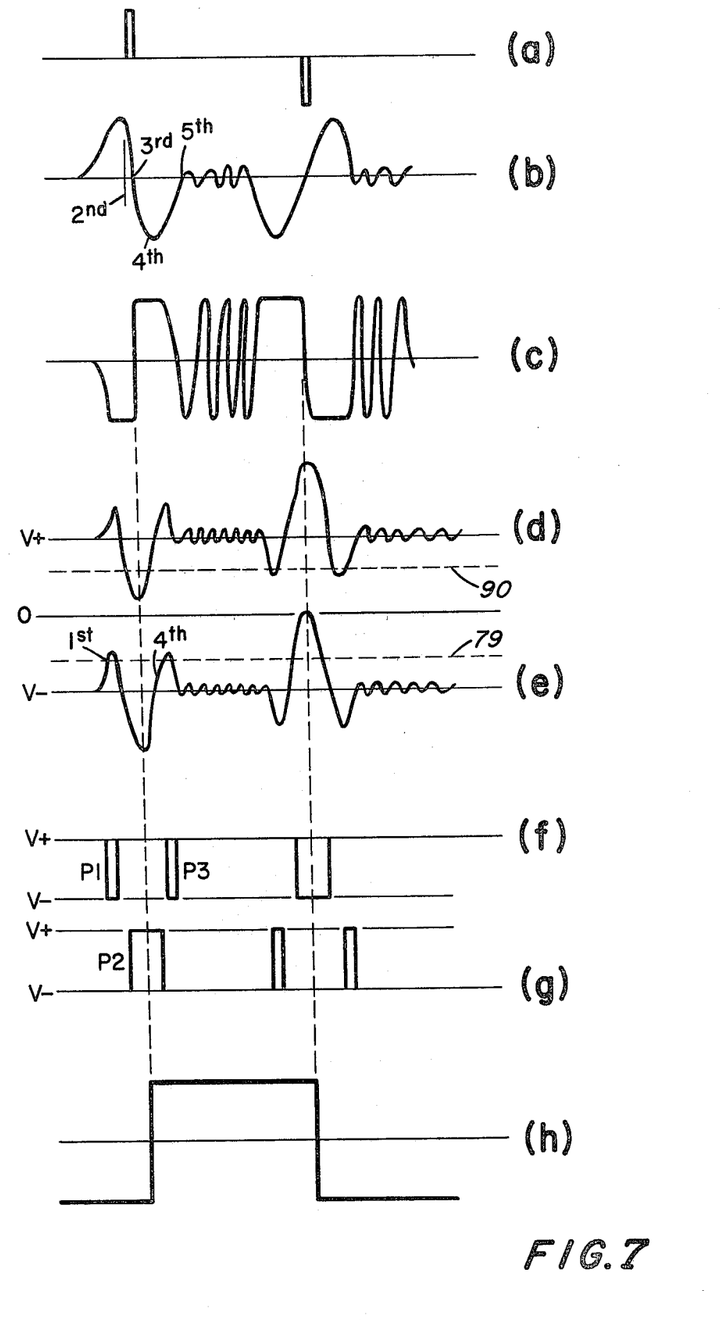
FIG. 7, consisting of a through h, illustrates voltage signals at various locations in the circuit shown in FIG. 6.

The pulses which represent the level transitions in the original PWM signal are illustrated in FIG. 7(a), and the playback signal from playback head 28 is shown in FIG. 7(b). The signal from the playback head 28, after amplification, is introduced to the playback circuit 30 at input 46. The amplified signal is then processed by a differential amplifier 48 which serves as the zero crossing detector 36 already described when reference was made to FIG. 4. Detector 36 changes state in dependence upon the polarity of its input, and issues an output signal which is illustrated in FIG. 7(c).

The input to zero crossing detector 35, illustrated in FIG. 7(b), is also the input to the time derivative circuit 38. The time derivative circuit 38, including capacitors 50 and 52, has its outputs displaced by respective power supply voltages V− and V+ acting through resistors 54 and 55, respectively, to produce voltage waveforms at "d" and "e" and illustrated in FIGS. 7(d) and 7(e).

The displaced differentiated signals serve as the outputs of the time derivative circuit 38 and are fed to the level detector circuit 40. These signals are impressed upon the respective bases of level detector transistors 58 and 60, through resistors 62 and 64, while transistors 58 and 60 receive collector bias by way of collector resistors 66 and 68, respectively. The output of the level detector transistors 58 and 60 serve as the inputs to the gate and memory circuit 44, through resistors 70 and 72. These signals appear at "f" and "g" in FIG. 6 and are illustrated in FIGS. 7(f) and 7(g), respectively. It should be noted that the portion of time derivative circuit 38 and level detector 40 including capacitor 50, transistor 58 and resistors 54, 62, 66 and 70 is the electrical complement of the portion including capacitor 52, transistor 60 and resistors 56, 64, 68 and 72.

Transistor 58 conducts when the voltage at point "d" is approximately 0.6 volts greater than negative bias voltage V−. This conduction level is indicated by the dotted line 74 superimposed on the waveform illustrated in FIG. 7(e), wherein it can be seen that transistor 58 conducts only when the amplitude of the derivative signal is large in a positive sense. It will be recalled that the derivative is large mainly in the region of the desired zero crossings, but to illustrate a practical situation, four spurious derivative signals are shown in FIGS. 7(d) and 7(e) to trigger the level detector 40.

Transistor 58 serves as a switch which controls the flow of current through collector resistor 66 which goes to positive bias voltage V+. The collector voltage on transistor 58 is applied through resistor 70 to the gate and memory circuit 44. The collector voltage appears at "f" and is illustrated in FIG. 7(f). Resistor 70 is much larger than is resistor 66 to minimize loading produced by the gate and memory circuit 44. Therefore, the voltage at the collector of transistor 58 is approximately V+ when transistor 58 is cut off, or non-conductive, and approximately V− when transistor 58 is conducting.

The operation of transistor 60 is similar to that of transistor 58, except that its input, being biased by V+ voltage, causes it to respond to large negative pulses in the differential signal. This is shown by the waveforms of FIGS. 7(d) and 7(g). It should be noted that either transistor 58 or transistor 60 may conduct, but not both simultaneously. The outputs of transistor 58 and 60 are fed to the gate and memory circuit 44 at junctions 74 and 76 intermediate diode pairs 78 and 80 and 82 and 84, respectively.

When transistors 58 and 60 are both cut off, the voltage at junction 74 of the gate and memory circuit 40 is approximately V+, while the voltage at junction 76 is approximately V−. This reverse biases diodes 78, 80, 82 and 84, which causes the voltage across a capacitor 86, serving as the memory element, to remain constant. As an example, the voltage across capacitor 86 could be negative at this instant, serving as the output 88 of the playback circuit 30, and as illustrated in FIG. 7(h).

The operation of the inventive circuit 30 will now be described by way of a specific example, commencing with the output 88 being negative. The first event of interest occurs when the amplitude of the derivative signal of FIG. 7(e) is large in a positive sense, in this case a spurious indication due to the fact that the threshold level 79 is exceeded.

When threshold level 79 is exceeded, transistor 58 begins to conduct and hence the voltage on its collector goes negative, issuing a pulse P1 shown in FIG. 7(f). This negative voltage reaches junction 74, connected to the collector of transistor 58 through resistor 70 and forward biases diode 78. Since the voltage at output 88 was negative prior to the occurrence of the pulse P1 shown in FIG. 7(f), the output voltage remains negative.

The second event which affects the operation of circuit 30 occurs when the playback signal of FIG. 7(b) starts through its first desired zero crossing. This results in a large, negative-going pulse in the derivative signal, shown in FIG. 7(d). The negative-going derivative pulse cuts off transistor 58 and, when its magnitude exceeds threshold 90 shown in FIG. 7(d), drives transistor 60 into conduction. This raises the voltage at the collector of transistor 60 to V+, as illustrated in FIG. 7(g) at P2, which voltage pulse is applied to junction 76 of gate 44 through resistor 72. Diode 82 becomes forward biased but, since the output impedance of the differential amplifier 48 is much lower than that of resistor 72, the potential at point "c" remains negative and the potential at junction 76 rises only slightly above that of point "c" due to the low forward voltage drop across diode 82. Since the potential at the input 46 is still positive, that at the output of amplifier 48 (point "c") remains negative.

The third event occurs at the instant when the playback signal of FIG. 7(b) passes through the desired zero crossing. This zero crossing causes the output of the operational amplifier or zero crossing detector 48 to shift instantaneously from negative to positive. Diode 82 therefore becomes reverse biased, and diode 84 becomes forward biased. Current then flows through transistor 60, resistor 72 and diode 84 to charge capacitor 86. If the time constant of this current path (determined by resistor 72 and capacitor 86) is made small, the change in voltage across capacitor 86 and hence in the output voltage at 88 occurs essentially instantaneously, and at the time of the desired zero crossing. This is shown in FIG. 7(h), wherein the output voltage goes from negative to positive. Subsequent to the zero crossing in the playback signal, the derivative of FIG. 7(d)

becomes less negative, and then threshold 90 is crossed, turning off transistor 60. The voltage at the collector of transistor 60 therefore again goes to V−, and reverse biases diodes 82 and 84. Capacitor 86 remains charged, and the output voltage at terminals 88 maintains its positive valve.

The fourth event is similar to the first, and occurs when the playback signal of FIG. 7(b) recovers from its negative-going zero crossing excursion. The derivative of the playback signal, illustrated in FIG. 7(e), again climbs positive and again, due to its amplitude, crosses threshold 79 and drives transistor 58 into conduction as shown at P3 in FIG. 7(f). This conduction causes the collector of transistor 58 to go negative and diode 78 to conduct. However, since the output impedance of the differential amplifier 48 is low compared with that of resistor 70, the potential at junction 74 cannot fall significantly, and so capacitor 86 remains positively charged. The fifth event is a spurious zero crossing in the signal shown in FIG. 7(b). The derivative is not of a magnitude to exceed thresholds 79 or 90, and therefore neither transistor 58 nor transistor 60 conducts. Points "f" and "g" experience no pulses, and rectifiers 80 and 84 remain reverse biased. Therefore, no current flows through the rectifiers to change the voltage on capacitor 86.

The circuit operation is not affected by the presence or absence of the first and fourth events. These events are illustrated only to show how the inventive circuit is insensitive to large derivatives unless accompanied by zero crossings in the playback signal. In the foregoing example, the sidelobe peaks of the derivative are large, and transistors 58 and 60 are driven into conduction. These peaks could be avoided entirely by raising the conduction thresholds of transistors 58 and 60. Event five illustrates the insensitivity of the inventive system to spurious zero crossings when not accompanied by large derivatives. The important feature of the inventive circuit is that the output changes state only upon the simultaneous occurrence of a pulse from either of transistors 58 or 60 and a zero crossing indication by differential zmplifier, or zero crossing detector 36.

During the second half of the cycle, there occurs a set of events complementary to the four which have been described in detail above, with the result that the voltage output at terminals 88 reverts to the negative state, but only at the precise occurrence of a desired zero crossing of the playback signal. In the second half of the cycle, the playback signal of FIG. 7(b) approaches the zero crossing in a positive-going direction. This reverses the roles of transistors 58 and 60, and diodes 78, 80, 82 and 84. The result is the issuance of a negative-going pulse at the collector of transistor 58 at a time corresponding to the output of the differential amplifier 48 again changing state. The result is that the output signal shown in FIG. 7(h) again goes negative.

Figure 8:
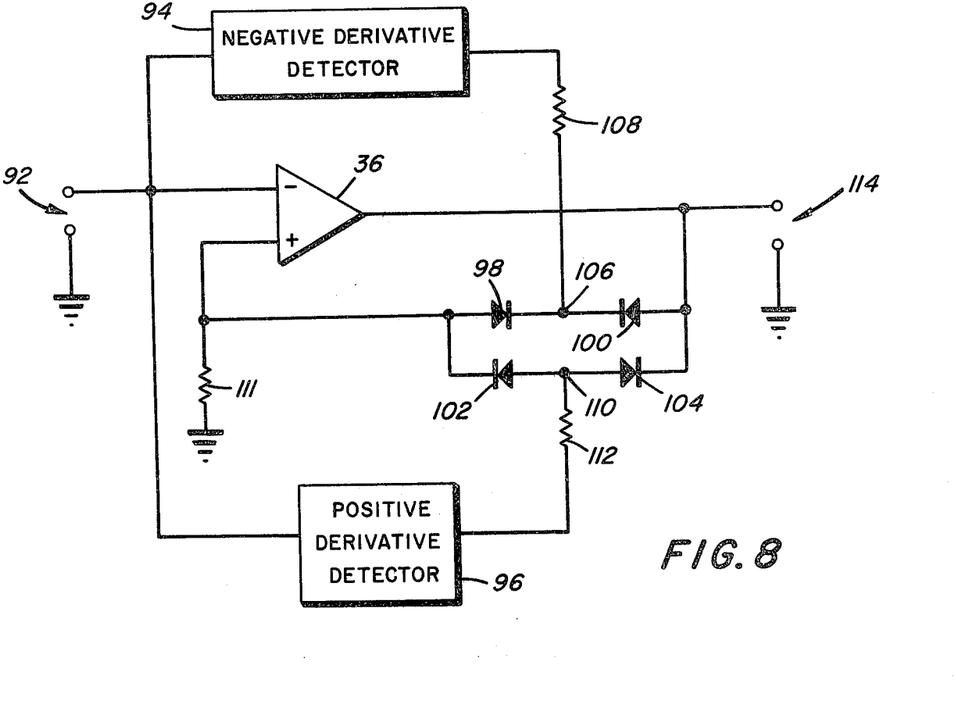
FIG. 8 is a combined circuit and block diagram showing another embodiment of the inventive playback circuit.

With reference now to FIG. 8, a block diagram of another embodiment of the inventive PWM signal playback circuit will be described. This embodiment differs from the first, which is illustrated in FIG. 6, principally in the end use of the derivative signal. In the circuit illustrated in FIG. 8, the operation of the zero crossing detector is suppressed unless a large derivative of the playback signal is present. That is, zero crossings are not detected unless the derivative is large. This operation should be compared with that of the circuit illustrated in FIG. 6, wherein the zero crossing detector 48 was active at all zero crossing, even spurious zero crossings, but its output was suppressed except when the derivative was large.

In FIG. 8, the input of the illustrated second embodiment is shown at 92, and leads, in parallel, to the inverting input of a zero crossing detector 36, a negative derivative detector 94 and a positive derivative detector 96. The output of the negative derivative detector 94 is designed to have a quiescent valve of a low voltage, −10 volts, for example. The corresponding quiescent output of the positive derivative detector 96 is designed to be +10 volts. Therefore, when no derivative signal is present which exceeds the thresholds of detectors 94 and 96, the four gate diodes 98, 100, 102 and 104 tend to be biased in the forward direction. The junction between diodes 98 and 100 is indicated at 106 and leads to the output of negative derivative detector 94 through a resistor 108. The junction 110 intermediate diodes 102 and 104 similarly connects to the positive derivative detector 96, through a resistor 112. The non-inverting input of zero crossing detector 36 is connected to ground through a resistor 111, and also to the junction between diodes 98 and 102. Resistors 108 and 112 are much smaller than is resistor 11, and much larger than the output impedance of zero crossing detector 36.

When the output of cross over detector 36 is high, +12 volts for example, and no high amplitude derivatives are detected, diode 100 conducts through resistor 108. The output of negative derivative detector 94 is −10 volts, as no negative derivative exceeding the threshold is detected. Because the impedance of resistor 108 is much higher than the output impedance of detector 36, junction 106 is at a positive potential on the order of +10 volts, which effectively reverse biases diode 98. The positive derivative detector 96 is also in its quiescent state, issuing an output of +10 volts, and therefore current flows through diode 102, and resistors 112 and 111, resistor 111 having an impedance much larger than that of resistor 112. The non-inverting input of zero crossing detector 36 is therefore maintained positive, at approximately +9 volts. If the input signal at 92 is limited to ±8 volts, less than the quiescent value at the non-inverting input of the detector 36, the detector 36 remains in its high state as long as neither positive detector 96 nor negative detector 94 detects high amplitude derivatives.

Figure 9:
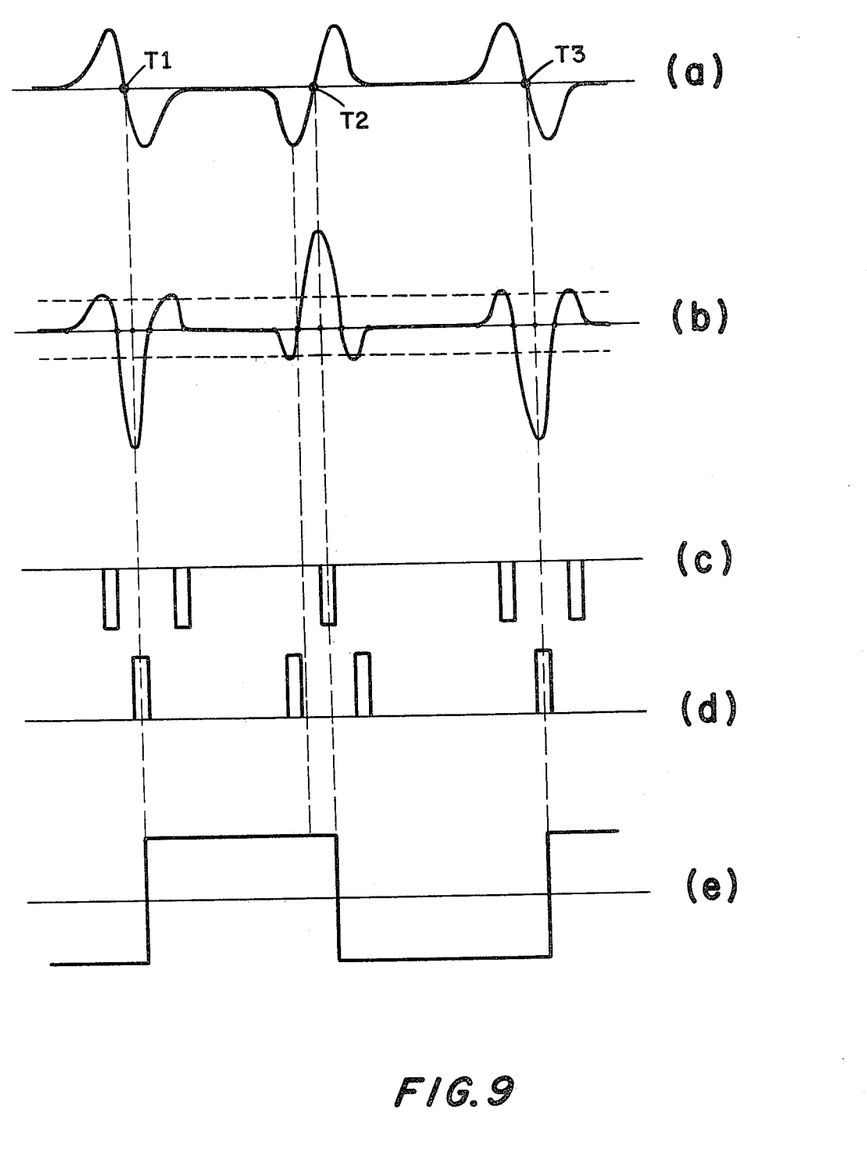
FIG. 9, consisting of a through e, illustrates voltage signals at various locations in the diagram shown in FIG. 8.

With reference to FIGS. 9(a) and 9(b), directing attention to a time just past the midway point between T1 and T2, it can be seen that the playback signal grows large and negative with a corresponding negative derivative. The negative derivative detector 94 therefore switches to a +10 volt output once the predetermined threshold [shown in phantom in FIG. 9(b)] is reached. None of the diodes are influenced, however, since diode 98 is already reverse biased and diode 100 is connected to the +12 volt output of zero crossing detector 36. Then, the derivative signal returns to zero and reverses sign as the time approaches T2. The output of the negative derivative detector 94 then returns to −10 volts.

When the derivative signal of FIG. 9(b) is large and positive, positive derivative detector 96 becomes active and switches its output reverse biases diodes 102 and 104 (already reverse biased by the +12 volt output of zero crossing detector 36). Only leakage currents flow through resistor 111 and the non-inverting input of detector zero crossing 36 is held near ground potential. The zero crossing detector 36 still has a negative input, however, until time T2 is reached.

At time T2, the playback signal shown in FIG. 9(a) goes through a desired zero crossing and becomes positive. Since the non-inverting input of detector 36 is now near ground potential, the zero crossing detector switches its output from +12 to −12 volts when the input 92 crosses through zero. Since junction 110 is at approximately −10 volts, diode 104 becomes forward biased and diode 102 is maintained reverse biased. Similarly, since the output of the negative derivative detector 94 is at −10 volts, diode 100 becomes reverse biased and the voltage at junction 106 falls to a negative value which forward biases diode 98 and drops the voltage at the non-inverting input of detector 36 from ground potential to approximately −9 volts. This voltage is more negative than the peak amplitude of input signal, and therefore prevents zero crossing detector 36 from switching out of its negative output state until time T3, the next desired zero crossing. The sequence of events at T3 is complementary to that described above at T2, and will therefore not be described in detail. The time of the transition of zero crossing detector 36 depends upon its sensitivity and the magnitude of the leakage current which biases the non-inverting input of detector 36.

It should be apparent that the respective circuits of FIGS. 6 and 8 operate on the same principle. Level transitions of a PWM signal are reproduced by evaluating the signal on the playback head of a magnetic tape device and by reacting to the simultaneous occurrence of zero crossings and high amplitude derivative signals.

Figure 10:
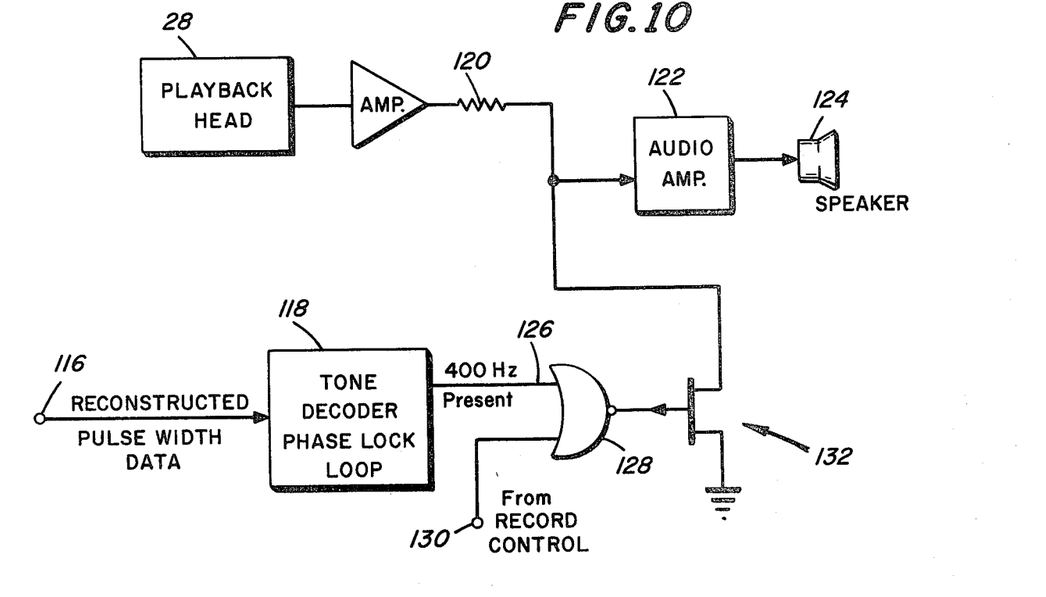
FIG. 10 is a combined circuit and block diagram showing the portion of the inventive circuit which enables automatic audio transmission in the playback mode.

With reference now to FIG. 10, there will be described a circuit for automatically responding to audio information previously recorded on magnetic tape. The reconstructed pulse width data is introduced to the circuit of FIG. 10 at 116, and serves as the input to a tone decoder phase lock loop circuit 118. The output of the tone decoder circuit 118 is fed to one input of a NOR gate circuit. The conventionally amplified audio signal is fed through resistor 120 to audio amplifier 122.

If the tone decoder circuit 118 detects the presence of the 400 Hz carrier in the reconstructed pulse width information, then a signal is issued on line 126 which feeds one input of a NOR gate 128, the other input of which is received from a recording mode switch control 130. The output of the NOR gate 128 biases the gate of a field effect transistor (FET) 132 which is connected between the resistor 120 and the input of the audio amplifier 122. FET 132 is in its conductive state when a strong 400 Hz tone is detected.

In operation, if the tone decoder circuit 118 detects the presence of the 400 Hz carrier, or if the tape recorded is in its recording mode, then a signal appears at one of the NOR gate inputs, and NOR gate 128 keeps FET 132 in its conductive state and thereby muting audio amplifier 122 by shunting the output of the playback preamplifier circuit to ground. If, on the other hand, no signal appears at terminal 130, indicating that the tape recorded is in its playback mode, and no signal appears at line 126, indicating the absence of the 400 Hz signal (in which case audio information is present on the tape), then NOR gate 128 issues a gating signal and field effect transistor 132 is switched to its non-conductive state. The output signal of the tone decoder 118 then passes through resistor 120, is amplified by audio amplifier 122 and made audible by speaker 124.

It will be recalled that the 400 Hz carrier is absent from the recorded tape when the operator is recording voice communication. Therefore, the absence of the 400 Hz carrier is automatically sensed by the circuit of FIG. 10, and the voice communication placed on tape by the operator can be heard from speaker 124 during the playback operation.

Above, specific embodiments of the present invention have been described. It should be appreciated, however, that these embodiments were described for purposes of illustration only, without any intention of limiting the scope of the present invention. Rather, it is the intention that the present invention be limited not by the above but only as is defined in the appended claims.

We claim:

1. A method for detecting zero crossings of a signal recorded on magnetic tape as a train of discrete pulses, the method comprising the steps of: moving the recorded magnetic tape past a playback head so a playback signal is generated by the playback head; sensing the precise instants when the playback signal crosses zero; developing a first time derivative signal from the playback signal; sensing high amplitude derivative signals which exceed a predetermined threshold level; determining the simultaneous occurance of sensed zero crossing and sensed high amplitude derivative signals; and developing an output signal having level transitions upon each determination of a simultaneous occurrence of a sensed zero crossing and a sensed high amplitude derivative signal.

2. An apparatus for reproducing a pulse width modulated signal recorded on magnetic tape in the form of a train of discrete pulses occurring at each level transition of the pulse width modulated signal, the apparatus comprising: a playback head for developing a playback signal derived from the train of pulses recorded on said magnetic tape; zero crossing detector means for sensing each zero crossing of said playback signal; time derivative means for developing a signal which is the derivative of said playback signal; threshold means for sensing high amplitude derivative signals which exceed a predetermined threshold level; means for determining the simultaneous sensing of zero crossings in the playback signal and high amplitude derivative signals; and means for generating an output signal having level transitions upon each determination of said simultaneous sensing.

3. The apparatus recited in claim 2, wherein the zero crossings of the playback signal are sensed by an operational amplifier the output of which changes state at each zero crossing.

4. The apparatus recited in claim 3, wherein the output of said operational amplifier is fed to a gate means, the gating of which is controlled by said threshold means.

5. The apparatus recited in claim 2, wherein said playback signal serves as an input to the operational amplifier; and further comprising means for preventing the output of said operational amplifier from changing state except upon the sensing of high amplitude derivative signals.

6. An apparatus for reacting to zero crossings of a desired type and for remaining insensitive to spurious zero crossings, the apparatus comprising: input means for receiving signals; detector means for receiving signals from said input means, for detecting zero crossings in the signals received, and for indicating the presence of such zero crossings; derivative means for receiving signals from said input means, for developing a first time derivative from the received signals, and for indicating the presence of derivatives exceeding a predetermined threshold; and means for sensing the condition of said detector means and said derivative means, and for responding to the simultaneous occurrence of a detected zero crossing and a derivative exceeding said predetermined threshold.

* * * * *